Figure 1:
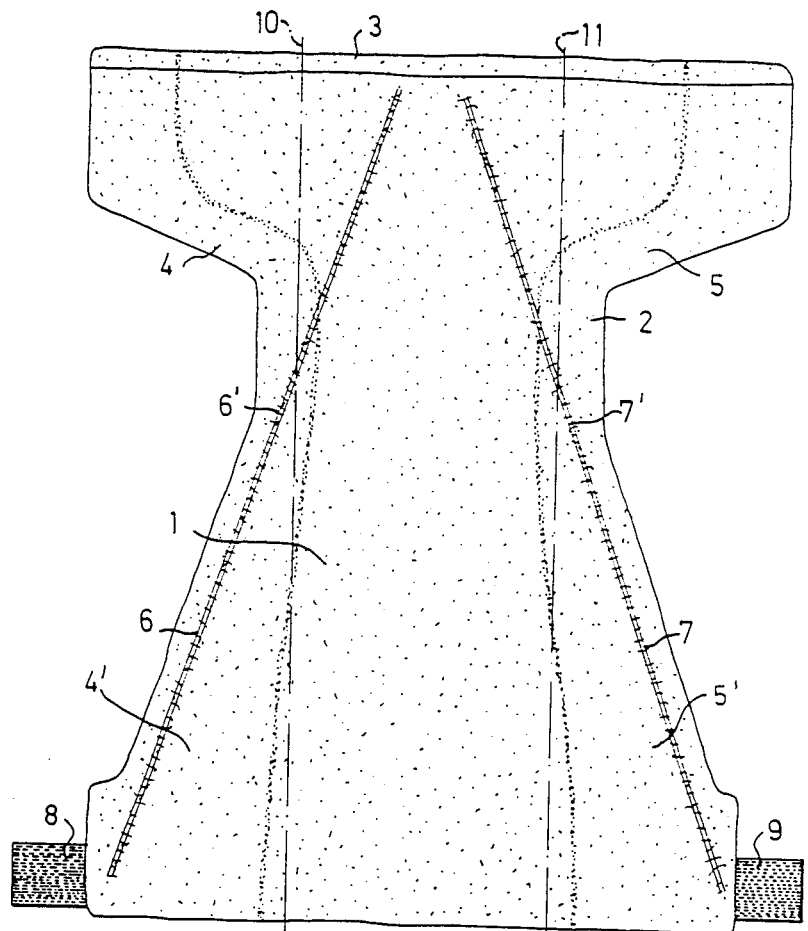

United States Patent [19]

Fröidh et al.

[11] Patent Number: 4,802,884
[45] Date of Patent: Feb. 7, 1989

[54] METHOD OF FOLDING INTO PACKAGES DISPOSABLE ABSORBENT ARTICLES, E.G. DIAPERS, IN CONNECTION WITH THE PRODUCTION THEREOF

[75] Inventors: Arne Fröidh, Stenungsund; Lennart Persson, Billdal, both of Sweden

[73] Assignee: Molnlycke AB, Goteborg, Sweden

[21] Appl. No.: 175,387

[22] PCT Filed: Jul. 10, 1987

[86] PCT No.: PCT/SE87/00333
§ 371 Date: Feb. 19, 1988
§ 102(e) Date: Feb. 19, 1988

[87] PCT Pub. No.: WO88/00441
PCT Pub. Date: Jan. 28, 1988

[30] Foreign Application Priority Data

Jul. 17, 1986 [SE] Sweden ............... 8603153

[51] Int. Cl.$^4$ ............... B65B 63/04
[52] U.S. Cl. ............... 493/339; 206/440; 493/394; 493/395; 493/406; 493/458; 493/960; 604/358
[58] Field of Search ............... 156/164, 212, 227, 229; 53/429, 117, 120; 604/378, 385 A, 385 R, 391, 400, 358, 379; 206/213, 438, 440, 805, 216; 383/49, 50, 112, 118; 493/339, 394, 395, 406, 405, 458, 960

[56] References Cited

U.S. PATENT DOCUMENTS

| | | |
|---|---|---|
| 2,693,439 | 11/1954 | Blanchard et al. |
| 3,963,029 | 6/1976 | Brooks. |
| 4,022,456 | 5/1977 | Hooper ............... 493/440 |
| 4,050,462 | 9/1977 | Woon ............... 604/385 |
| 4,585,448 | 4/1986 | Enloe ............... 604/378 |
| 4,674,135 | 6/1987 | Greene ............... 206/213 |

FOREIGN PATENT DOCUMENTS

| | | | |
|---|---|---|---|
| 1440905 | 6/1976 | United Kingdom | 493/458 |
| 2127674 | 4/1984 | United Kingdom. | |

*Primary Examiner*—Michael W. Ball
*Assistant Examiner*—Steven D. Maki
*Attorney, Agent, or Firm*—Young & Thompson

[57] ABSTRACT

A method of folding into packages, in connection with the manufacture thereof, disposable absorbent articles such as diapers or incontinence protectors comprising an absorbent body (1) enclosed in a casing extending laterally beyond the absorbent body and having casing portions intended to seal around the abdomen of the wearer, as well as elastic leg bands or threads (6, 7) affixed to the casing with portions (6', 7') extending at least partially along either side edge of the article at a distance beyond the absorbent body. The ends of the article are folded in with approximately equal lengths toward the mid-section of the article, which is thereafter folded together in the same direction into a four-folded state. The elastic portions (6', 7') at the center of the article are simultaneously held laterally stretched so as to encompass the laterally positioned article ends. The folded article, upon release of these elastic portions, is held together thereby in the state of a compact, four-folded package.

2 Claims, 2 Drawing Sheets

METHOD OF FOLDING INTO PACKAGES DISPOSABLE ABSORBENT ARTICLES, E.G. DIAPERS, IN CONNECTION WITH THE PRODUCTION THEREOF

The present invention relates to a method of folding into packages, in connection with the manufacture thereof, disposable absorbent articles such as diapers, incontinence protectors or the like comprising an absorbent body enclosed in a casing which extends laterally beyond the absorbent body and which has casing portions intended to seal around the abdomen of the wearer, as well as elastic leg means in the form of elastic bands, threads or the like which are affixed to the casing with portions extending at least partially along either side edge of the article at a distance beyond the absorbent body.

In the past, disposable absorbent bodies made of cotton or cellulose were used in combination with liquid-tight plastic backings or plastic pants intended for multiple use. These absorbent bodies had a rectangular shape and the manufacture thereof was a quite simple process.

The demands on comfort, function and easy handling have however lead to products of a more sophisticated nature. The majority of consumers have also gradually changed over to the use of completely disposable articles. Such products have a central absorbent body which normally consists of so-called fluff pulp, or of highly absorbent material possibly in combination with fluff pulp. This absorbent body is enclosed in a casing composed of a liquid permeable outer layer made of fiber fabric for example on the side facing the body of the wearer during use of the article, and a liquid impermeable layer, generally a plastic film, on the opposite side. The casing extends laterally beyond the absorbent body and is provided with elastic members serving to seal around the legs of the wearer. In normal cases, the absorbent body is non-rectangular but is instead made to conform to the bodily shape of the wearer, for which purpose it may be hourglass-shaped with a center portion made narrower in relation to the end portions, or it can be T-shaped with a wider portion fitting snugly to the wearer's abdomen and being located forwardly of the crotch portion.

The methods of producing completely disposable articles of this type however require quite advanced and thus expensive automated equipment. In order to keep the manufacturing costs of such articles at a competitive level in relation to simple, rectangular absorbent bodies used in combination with plastic backings, there is actually demanded a high manufacturing speed. Also, the development of such products leads to articles having a smoother and more pleasant finish, which are factors adding to the material costs so that in order to make the production profitable enough, the manufacturing rate has to be accelerated to a still higher degree.

Moreover, absorbent articles of the afore-described kind are comparatively voluminous and must therefore be folded and compressed before being inserted in multi-piece packages.

Since the articles in question are manufactured in a continuous path from which individual articles are cut prior to folding and packaging, folding and packaging of these separate items will be most difficult to carry out at such extreme manufacturing rates. As a consequence, frequently occurring production disturbances are normal in conventional folding and packaging plants and give rise to manufacturing stoppage, which in turn leads to poor operational economy. In particular, the portions of the casing provided with elastic members and projecting beyond the side edges of the absorbent body are elements giving rise to serious problems in the folding and handling process, and operational disturbances are most frequently caused by such casing portions getting dislocated and hooked.

The present invention has for its object to teach a novel and simplified method of folding, which can be employed in connection with manufacture of the disposable articles mentioned in the introduction for eliminating the operational disturbances caused by the casing portions projecting from each individual article.

To this end, the method according to the invention is primarily characterized in that the ends of the article are folded in with approximately equal lengths towards the article mid-section, whereafter the article is folded together in the same direction into a four-folded state. During the folding sequence, the elastic portions in the center of the article are held laterally stretched so as to emcompass the laterally positioned article ends, and upon release of said elastic portions the folded article is held together thereby in the form of a compact, four-folded package.

According to a suitable embodiment of folding bodily adapted diapers of hourglass or T-shape for example, which have at least at one of their ends casing and absorbent body sections laterally widened in relation to the crotch portion, the invention is characterized in that said widened sections are first laterally folded in to assume a substantially rectangular shape, whereafter the article is bent together into a four-folded state, said widened end sections as well being locked inside at least the centrally located elastic portions of the article.

According to the inventive method of folding, the natural elasticity of the article subjected to folding is utilized to retain the casing portion of the article projecting from the absorbent body during simultaneous formation of a solidly compacted one-piece package, which is easily handled when being packed into larger packaging units.

Figure 2:
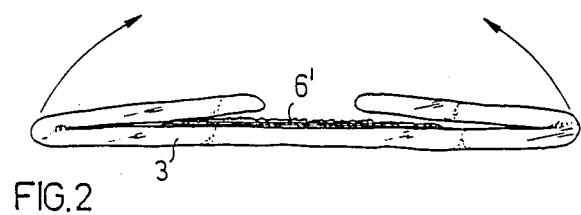
Figure 3:
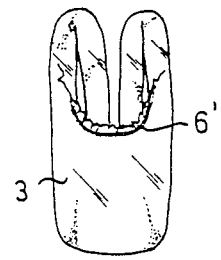

The invention will be described in more detail below with reference to an exemplary embodiment illustrated in the drawings, of which FIG. 1 shows a disposable diaper provided with elastic members and seen in a flat, extended state, FIG. 2 shows the inventive method of folding, whereas FIG. 3 is a lateral view of the diaper according to FIGS. 1 and 2 as folded into its final packaging state.

The disposable diaper illustrated in FIG. 1 has a T-shaped absorbent core of cellulose fluff pulp. The absorbent core is enclosed in a casing composed of a liquid permeable outer layer 2 of fiber fabric and intended to lie next to the wearer's body, combined with a liquid impermeable outer layer 3 of polyurethane on the opposite side of the absorbent body. The two outer layers 2, 3 extend with portions 4, 5 laterally beyond the absorbent core where they are joined together As can be seen from FIG. 1, said portions 4, 5 extend in a direction towards the rear end of the diaper and laterally outwards at a gradually increasing distance from either side edge of the absorbent body while forming substantially triangular flaps 4', 5' intended to seal around the wearer's bottom during use of the diaper. Elastic members in the form of elastic threads 6, 7 are applied under pretension into a V-shaped pattern across the diaper. These elastic members have the function of sealing around the wearer's bottom.

The manner of applying the elastic threads into a V-shaped pattern according to FIG. 1 has been selected with regard to conformability of the elastic to the human body. The elastic threads intersect the side edges of the absorbent body substantially at the diaper crotch area so as to prevent the elastic members from cutting into the wearer's skin in the crotch area.

Furthermore, the diaper shown is provided with attachment means in the form of tape tabs 8, 9 which are securely fixed to the rear end of the diaper. During application of the diaper, freely exposed portions of said tape coated with adhesive are affixed to the outer polyethylene layer 3 on the outside of the diaper front end.

Diapers according to FIG. 1 are manufactured in a continuous path at a high speed, and so far the handling and packaging process has been difficult to carry out in an efficient manner.

The concept of the inventive method is to have the diaper folded into a compact and easily handled item prior to packaging, said item being held together in its folded state by means of its associated elastic members 6, 7.

There have been indicated with dash-dotted lines in FIG. 1 two folding lines 10, 11. On implementation of the inventive method, the side flaps located beyond said folding lines are folded in towards the center of the diaper which is thereby rendered an essentially rectangular shape, the mid-sections 6', 7' of the elastic threads simultaneously being stretched out to the sides during the entire folding operation.

In the next sequence and in accordance with the invention, the two opposing diaper ends are folded in towards one another with substantially equal lengths and further towards the diaper mid-section so as to assume the state illustrated in FIG. 2. The diaper is then folded together as shown by the arrows in FIG. 2, the folded diaper portions now lying laterally embraced by the stretched-out elastic thread portions 6', 7'. Upon release of said thread portions, the folded diaper is held elastically compressed in a compact four-folded package according to FIG. 3.

In this finally folded state and with all diaper flaps being tucked inside the elastic, the diapers will be easily handled, and continued packaging can proceed undisturbed by any projecting diaper flap.

The diaper is folded so that the plastic film will form the outside of the package shown in FIG. 3. In this manner there is also obtained a hygienic one-piece package which is easy to carry along.

The invention is not restricted to the abovedescribed exemplary embodiment, since a plurality of modifications are conceivable within the scope of the patent claims.

The shape of the diaper is thus not limited to that exemplified herein.

We claim:

1. A method of folding into packages, in connection with the manufacture thereof, disposable absorbent articles such as diapers, or incontinence protectors comprising an absorbent body (1) enclosed in a casing extending laterally beyond the absorbent body and having casing portions intended to seal around the abdomen of the wearer, as well as elastic leg means in the form of elastic bands or threads (6,7) affixed to the casing with portions (6',7') extending at least partially along either side edge of the article at a distance beyond the absorbent body, characterized in that the ends of the article are folded in with approximately equal lengths towards the mid-section of the article which is thereafter folded together in the same direction into a four-folded state, the elastic portions (6',7') at the center of the article simultaneously being held laterally stretched so as to encompass the laterally positioned article ends, the folded article upon release of said elastic portions being held together thereby in the state of a compact, four-folded package.

2. A method according to claim 1 of folding articles of the type having, at least at one of their ends, casing and absorbent body sections which are laterally widened in relation to the crotch portion, characterized in that said widened sections are first laterally folded in to assume a substantially rectangular shape, whereafter the article is bent together into a four-folded state, said widened end sections as well being locked inside at least the centrally located elastic portions (6',7') of the article.

* * * * *